United States Patent
Nakamura et al.

(10) Patent No.: US 9,959,614 B2
(45) Date of Patent: May 1, 2018

(54) IMAGE PROCESSING DEVICE AND METHOD

(71) Applicant: FUJIFILM Corporation, Tokyo (JP)

(72) Inventors: Keigo Nakamura, Ashigarakami-gun (JP); Tomoyuki Takahashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 18 days.

(21) Appl. No.: 15/082,124

(22) Filed: Mar. 28, 2016

(65) Prior Publication Data

US 2016/0210744 A1  Jul. 21, 2016

Related U.S. Application Data

(63) Continuation of application No. PCT/JP2014/004890, filed on Sep. 24, 2014.

(30) Foreign Application Priority Data

Sep. 30, 2013  (JP) .................................. 2013-203048

(51) Int. Cl.
*G06K 9/00* (2006.01)
*G06T 7/00* (2017.01)
(Continued)

(52) U.S. Cl.
CPC .......... *G06T 7/0012* (2013.01); *A61B 6/5211* (2013.01); *G06T 5/009* (2013.01);
(Continued)

(58) Field of Classification Search
None
See application file for complete search history.

(56) References Cited

U.S. PATENT DOCUMENTS 7,978,921 B1 * 7/2011 Donovan .................. G06T 9/00
382/233
8,134,532 B2 * 3/2012 Baba .................... G09G 3/3406
345/102

(Continued)

FOREIGN PATENT DOCUMENTS

JP  2000-155838 A   6/2000
JP  2003-310589 A  11/2003

(Continued)

OTHER PUBLICATIONS

Communication dated Sep. 13, 2016, from the Japanese Patent Office in counterpart application No. 2013-203048.
Written Opinion for PCT/JP2014/004890 dated Dec. 2, 2014.
International Search Report for PCT/JP2014/004890 dated Dec. 2, 2014.

*Primary Examiner* — Soo Park
(74) *Attorney, Agent, or Firm* — Sughrue Mion, PLLC (57) ABSTRACT

A first concentration range, which is a concentration range of a region of interest, and an output concentration range are determined in an input image. A compression table for compressing a dynamic range of the input image is generated on the basis of the first concentration range and the output concentration range. The first concentration range is changed at a predetermined ratio with respect to the changed output concentration range to determine a second concentration range. A new compression table is generated on the basis of the changed output concentration range and the second concentration range. The dynamic range of the input image is compressed using the new compression table.

7 Claims, 7 Drawing Sheets

(51) Int. Cl.

| | |
|---|---|
| *A61B 6/00* | (2006.01) |
| *G06T 5/00* | (2006.01) |
| *H04N 1/407* | (2006.01) |
| *G06T 5/40* | (2006.01) |
| *H04N 19/98* | (2014.01) |
| *H04N 19/17* | (2014.01) |
| *H04N 19/172* | (2014.01) |
| *H04N 19/12* | (2014.01) |
| *H04N 19/167* | (2014.01) |

(52) U.S. Cl.
CPC ............ G06T 5/40 (2013.01); H04N 1/4074 (2013.01); H04N 19/98 (2014.11); *G06T 2207/10116* (2013.01); *H04N 19/12* (2014.11); *H04N 19/167* (2014.11); *H04N 19/17* (2014.11); *H04N 19/172* (2014.11)

(56) References Cited

U.S. PATENT DOCUMENTS

| | | | |
|---|---|---|---|
| 8,861,878 B2* | 10/2014 | Iwaki | H04N 1/407 382/162 |
| 2005/0254707 A1 | 11/2005 | Takahashi | |
| 2009/0180714 A1* | 7/2009 | Takahashi | G06T 5/009 382/307 |
| 2009/0290040 A1* | 11/2009 | Du | G06T 5/009 348/222.1 |
| 2011/0216834 A1* | 9/2011 | Zhou | H04N 7/12 375/240.24 |

FOREIGN PATENT DOCUMENTS

| | | |
|---|---|---|
| JP | 2005-319214 A | 11/2005 |
| JP | 2009-169592 A | 7/2009 |
| JP | 2013-138913 A | 7/2013 |

* cited by examiner

IMAGE PROCESSING DEVICE AND METHOD

CROSS-REFERENCE TO RELATED APPLICATIONS

This application is a Continuation of PCT International Application No. PCT/JP2014/004890 filed on Sep. 24, 2014, which claims priority under 35 U.S.C. § 119(a) to Japanese Patent Application No. 2013-203048 filed on Sep. 30, 2013. Each of the above applications is hereby expressly incorporated by reference, in its entirety, into the present application.

BACKGROUND OF THE INVENTION

1. Field of the Invention

The present invention relates to an image processing device and an image processing method which perform a dynamic range compression process for an image such as a radiological image.

2. Description of the Related Art

A radiological image used in an image diagnosis is acquired by an imaging process of a computed radiography (CR) system or an imaging process using a radiation detector (FPD). The dynamic range of the acquired radiological image is very wide. In a case in which an output device reproduces the radiological image with a wide dynamic range, the dynamic range of the image is compressed so as to fall within a concentration range which can be output by the output device, in order to prevent the occurrence of blown-out highlights in a bright portion of the image and the occurrence of blocked-up shadows in a dark portion of the image. For example, JP2000-155838A discloses a method which sets the concentration range (latitude; hereinafter, referred to as an L value) of an image to which a range from the minimum value to the maximum value of the concentration scale of an output device is allocated, sets the concentration range of a region of interest which is included in the image and is to be observed as a concentration range which is not subjected to a dynamic range compression process, and calculates dynamic range compression parameters (for example, a compression table) on the basis of the set concentration ranges. JP2003-310589A discloses a method which changes dynamic range compression parameters, depending on at least one of information about the dynamic range of a subject and information about a captured part of the subject.

JP2013-138913A discloses a method which, when dynamic range compression parameters are set and the gradient of gradation is corrected, corrects a concentration range for compressing the dynamic range according to the corrected gradation.

SUMMARY OF THE INVENTION

In some cases, the image of which the dynamic range has been compressed does not have a desired contrast or blown-out highlights or blocked-up shadows occur in the image. In this case, a user, such as a radiology technician or a doctor, needs to manually adjust the parameters in the displayed image. For example, in a case in which the user wants to emphasize the contrast of the region of interest in the image, the user decreases the L value. In contrast, in a case in which the user wants to decrease the contrast of the region of interest or blown-out highlights or blocked-up shadows occur in the region of interest, the user needs to increase the L value. In this case, in the method disclosed in JP2000-155838A, it is considered that, even if the L value is changed, the concentration range of the region of interest which is not subjected to the dynamic range compression process is not changed and the dynamic range compression parameters are changed.

However, the parameters before the change are set such that a concentration balance between an output concentration range and the concentration range of the region of interest is optimized. Therefore, when the parameters are changed, without changing the concentration range of the region of interest which is not subjected to the dynamic range compression process, the concentration balance between the output concentration range and the concentration range of the region of interest is broken and a desired contrast is not obtained from the region of interest or blown-out highlights or blocked-up shadows appear in a region of the image. As a result, there is a concern that an image with a desired quality will not be obtained.

For this reason, the concentration range of the region of interest being changed with a change in the L value is considered. However, when the concentration range of the region of interest is changed, it is necessary to adjust the maximum value and the minimum value of the concentration range of the region of interest in addition to the maximum value and the minimum value of the L value. As a result, the operation becomes very complicated. In addition, it is difficult to know how to change the concentration range in which the dynamic range is not compressed, with a change in the L value, in order to obtain an image with a desired quality.

The invention has been made in view of the above-mentioned problems and an object of the invention is to provide a technique which is capable of obtaining an image with a desired quality, using a simple structure, when performing a dynamic range compression process for an image such as a radiological image.

According to an aspect of the invention, there is provided an image processing device that performs a dynamic range compression process for an input image. The image processing device includes: first concentration range determination means for determining a first concentration range which is a concentration range of a region of interest in the input image; output concentration range determination means for determining an output concentration range in the input image; compression table generation means for generating a compression table for compressing a dynamic range of the input image on the basis of the first concentration range and the output concentration range; compression processing means for compressing the dynamic range of the input image using the compression table; and second concentration range determination means for changing the first concentration range at a predetermined ratio with respect to the changed output concentration range to determine a second concentration range. The compression table generation means generates a new compression table on the basis of the changed output concentration range and the second concentration range. The compression processing means compresses the dynamic range of the input image using the new compression table.

The "concentration range of the region of interest" means a concentration range which is not subjected to a dynamic range compression process.

The "output concentration range" means, for example, a concentration range of an image to which a range from the minimum value to the maximum value of the concentration scale of an output device is allocated, that is, an L value. The range is not limited to the minimum value and the maximum value of the concentration scale. For example, a value that is greater than the minimum value by a predetermined value or a value that is less than the maximum value by a predetermined value may be used instead of the minimum value or the maximum value.

In the image processing device according to the above-mentioned aspect of the invention, the second concentration range determination means may determine the second concentration range on the basis of a predetermined reference concentration.

In the image processing device according to the above-mentioned aspect of the invention, the predetermined ratio may be at least one of a ratio of a value from a minimum value of the first concentration range to the predetermined reference concentration to a value from a minimum value of the output concentration range to the predetermined reference concentration and a ratio of a value from the predetermined reference concentration to a maximum value of the first concentration range to a value from the predetermined reference concentration to a maximum value of the output concentration range.

In the image processing device according to the above-mentioned aspect of the invention, the predetermined reference concentration may be a median of the output concentration range.

In the image processing device according to the above-mentioned aspect of the invention, the predetermined reference concentration may be a concentration value which is changed to a target concentration in the input image.

According to another aspect of the invention, there is provided an image processing method that performs a dynamic range compression process for an input image. The method includes: determining a first concentration range which is a concentration range of a region of interest in the input image; determining an output concentration range in the input image; generating a compression table for compressing a dynamic range of the input image on the basis of the first concentration range and the output concentration range; compressing the dynamic range of the input image using the compression table; changing the first concentration range at a predetermined ratio with respect to the changed output concentration range to determine a second concentration range; generating a new compression table on the basis of the changed output concentration range and the second concentration range; and compressing the dynamic range of the input image using the new compression table.

According to still another aspect of the invention, there is provided a program that causes a computer to perform the image processing method according to the invention.

According to the invention, the first concentration range is changed at a predetermined ratio with respect to the changed output concentration range to determine the second concentration range. A new compression table is generated on the basis of the changed output concentration range and the second concentration range. The dynamic range of the input image is compressed using the new compression table. Therefore, the user changes only the output concentration range to change the concentration range of the region of interest in which the dynamic range is not compressed. As a result, it is possible to reduce the burden of the operation on the user. In addition, since the second concentration range is determined by changing the first concentration range at a predetermined ratio with respect to the changed output concentration range, it is possible to appropriately adjust the concentration balance between the changed output concentration range and the second concentration range according to a predetermined ratio. Since the dynamic range of the input image is compressed using a new compression table, it is possible to optimally adjust the concentration balance between the output concentration range and the concentration range of the region of interest, similarly to the method using the compression table before the change. As a result, it is possible to obtain an image with a desired contrast in which without blown-out highlights or blocked-up shadows do not occur.

In particular, since the predetermined ratio is at least one of the ratio of the value from the minimum value of the first concentration range to the predetermined reference concentration to the value from the minimum value of the output concentration range to the predetermined reference concentration and the ratio of the value from the predetermined reference concentration to the maximum value of the first concentration range to the value from the predetermined reference concentration to the maximum value of the output concentration range, the concentration balance between the changed output concentration range and the second concentration range can be the same as the concentration balance between the output concentration range before the change and the first concentration range. Therefore, it is possible to optimally adjust the concentration balance between the output concentration range and the concentration range of the region of interest. As a result, it is possible to obtain an image with a desired contrast.

DESCRIPTION OF THE PREFERRED EMBODIMENTS

Figure 1:
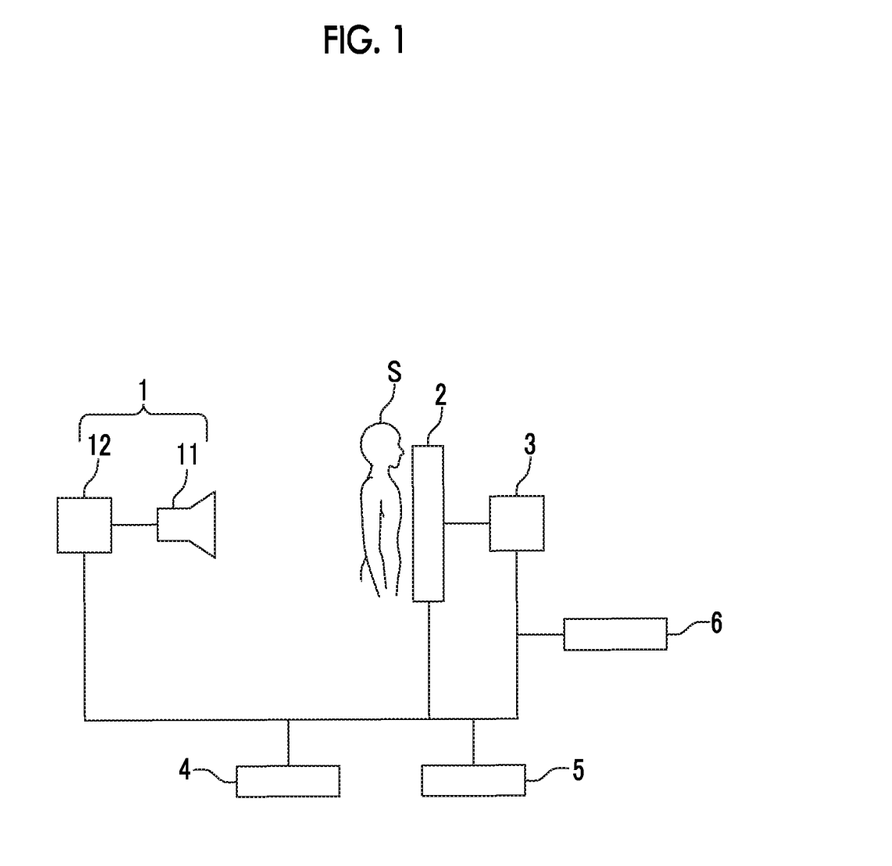
FIG. 1 is a block diagram schematically illustrating the structure of a radiological image diagnosis system to which an image processing device according to an embodiment of the invention is applied.

Hereinafter, an embodiment of the invention will be described with reference to the drawings. FIG. 1 is a block diagram schematically illustrating the structure of a radiological image diagnosis system to which an image processing device according to the embodiment of the invention is applied. As illustrated in FIG. 1, the radiological image diagnosis system includes a radiation generation device 1, a radiation detector 2, an image processing device 3, an imaging control device 4 and an input unit 5. The radiation generation device 1 and the radiation detector 2 are provided so as to be opposite to each other with a subject S interposed therebetween. The imaging control device 4 is connected to the radiation generation device the radiation detector 2, the image processing device 3, and the input unit 5. The radiation detector 2 is connected to the image processing device 3.

The radiation generation device 1 includes a radiation tube 11 that emits radiation and a high voltage generator 12 that applies a tube voltage to the radiation tube 11, and can irradiate the subject S with radiation under the control of the imaging control device 4. The imaging control device 4 controls the setting of imaging conditions, such as the tube voltage, a tube current, and an irradiation time, or operations based on the imaging conditions, on the basis of an input from the input unit 5.

The radiation detector 2 stores radiological image information including radiation which passes through the subject S as an electrostatic latent image, reads the stored electrostatic latent image, and detects a radiation transmissivity distribution as a radiological image. The radiation detector 2 may have any structure as long as it detects radiation and outputs the detected radiation as image information. For example, the radiation detector 2 may be a TFT-type solid-state detector or an optical-reading-type solid-state detector.

The image processing device 3 is a computer that includes, for example, a keyboard or a mouse (that is, the input unit 5) which receives an input from the operator, a display unit 6, such as a high definition liquid crystal display which displays images, and a main body which includes a CPU, a memory, a hard disk, and a communication interface. The image processing device 3 has a function of performing various types of image processing including a gradation process for the radiological image.

The input unit 5 is an interface which is, for example, a keyboard, a mouse, or a touch-panel-type input unit and receives various inputs required for the radiological image diagnosis system, such as an imaging instruction from the operator, an image processing instruction, and the designation of an imaging menu.

Figure 2:
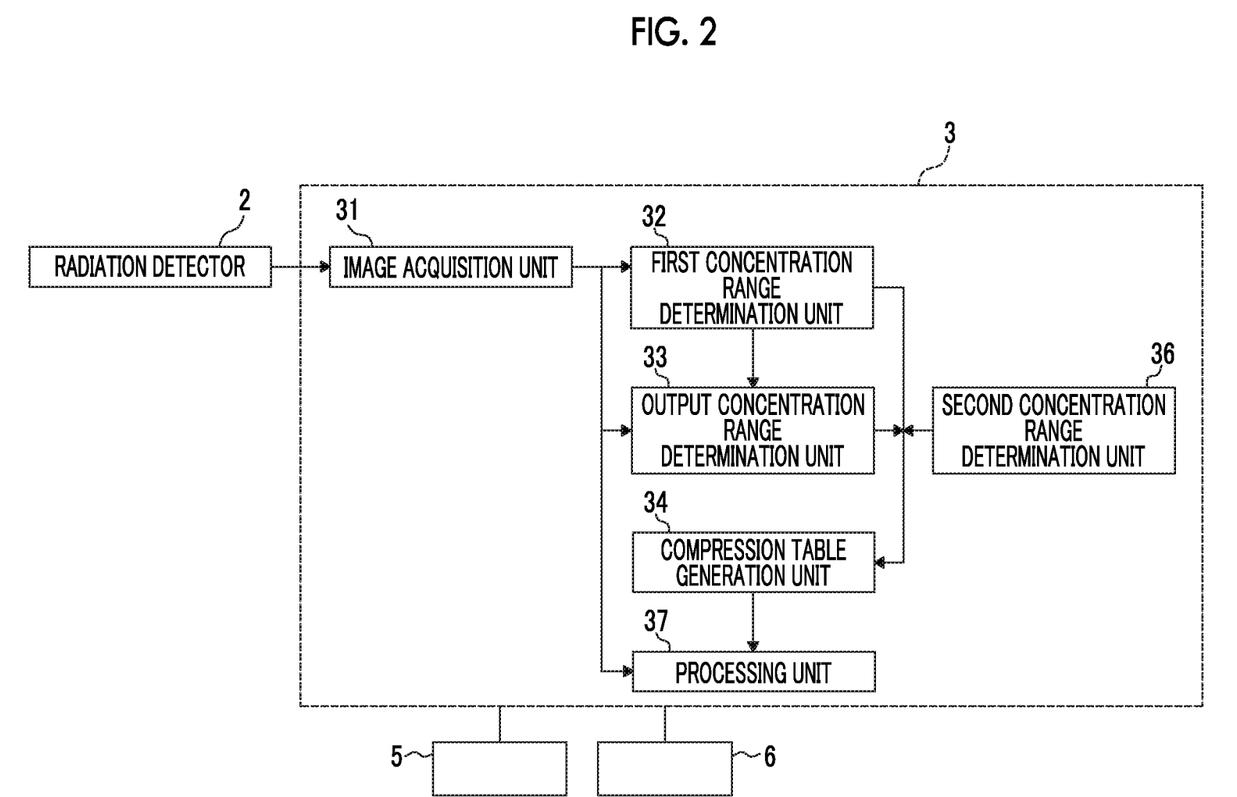
FIG. 2 is a block diagram schematically illustrating the structure of the image processing device.

FIG. 2 is a block diagram schematically illustrating the structure of the image processing device 3. As illustrated in FIG. 2, the image processing device 3 includes an image acquisition unit 31, a first concentration range determination unit 32, an output concentration range determination unit 33, a compression table generation unit 34, a second concentration range determination unit 36, and a processing unit 37.

The image acquisition unit 31 acquires a radiological image G0 (input image) acquired by the radiation detector 2 as digital data.

The first concentration range determination unit 32 determines a first concentration range which is a concentration range of a region of interest in the radiological image G0. First, the first concentration range determination unit 32 creates a histogram of the radiological image G0. Then, the first concentration range determination unit 32 determines the concentration range of the region of interest to be observed in the radiological image G0 as the first concentration range. The first concentration range is a concentration range in which a dynamic range is not compressed by a dynamic range compression process which will be described below. The first concentration range determination unit 32 removes a void portion which is acquired by direct irradiation in the radiological image G0, a subject region which is adjacent to the void portion with a predetermined width therebetween, and a non-irradiation region which is other than an irradiation region from the radiological image G0. Then, the first concentration range determination unit 32 determines, as the first concentration range, a range from the minimum value to the maximum value of a concentration value in the radiological image G0 from which the void portion, the subject region which is adjacent to the void portion with a predetermined width therebetween, and the non-irradiation region have been removed. The user, such as a radiology technician or a doctor, may manually set the first concentration range, using the input unit 5. Alternatively, a feature amount Din, which will be described below, may be calculated and the first concentration range may be set on the basis of the feature amount Din.

Figure 3:
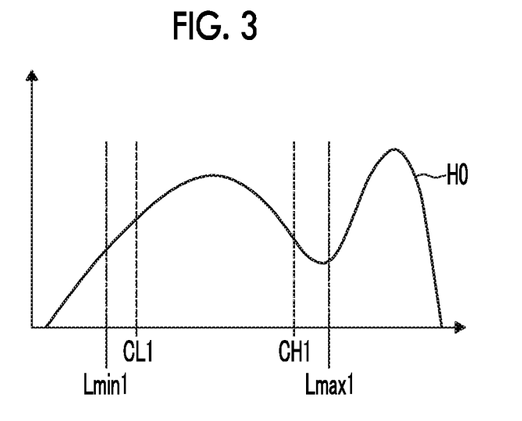
FIG. 3 is a diagram illustrating the determination of a first concentration range and an output concentration range.

FIG. 3 is a diagram illustrating the determination of the first concentration range and an output concentration range which will be described below. In FIG. 3, the determination will be described using the histogram of the radiological image G0. In FIG. 3, the horizontal axis indicates the concentration value and the vertical axis indicates the frequency of the concentration value. As illustrated in FIG. 3, a range from a minimum value CL1 to a maximum value CH1 in the range from which the void portion, the subject region which is adjacent to the void portion with a predetermined width therebetween, and the non-irradiation region have been removed in the histogram H0 is determined as the first concentration range.

The output concentration range determination unit 33 determines the output concentration range, that is, an L value, in the radiological image G0. The L value means the concentration range of the radiological image G0 to which a range from the minimum value to the maximum value of the concentration scale of an output device (in this embodiment, the display unit 6) is allocated. The output concentration range determination unit 33 determines, for example, the minimum value and the maximum value of a main histogram in the histogram H0 as a minimum value Lmin1 and a maximum value Lmax1 of the output concentration range, respectively. Therefore, the concentration range of the main histogram in the histogram H0 is allocated to the minimum value and the maximum value of the gradation of the display unit 6. In addition, a value that is greater than the minimum value of the histogram H0 by a predetermined percent (for example, several percent) in the entire concentration range of the histogram H0 can be used as the minimum value of the main histogram. Similarly, a value that is smaller than the maximum value of the histogram H0 by a predetermined percent (for example, several percent) in the entire concentration range of the histogram H0 can be used as the maximum value of the main histogram.

Figure 4:
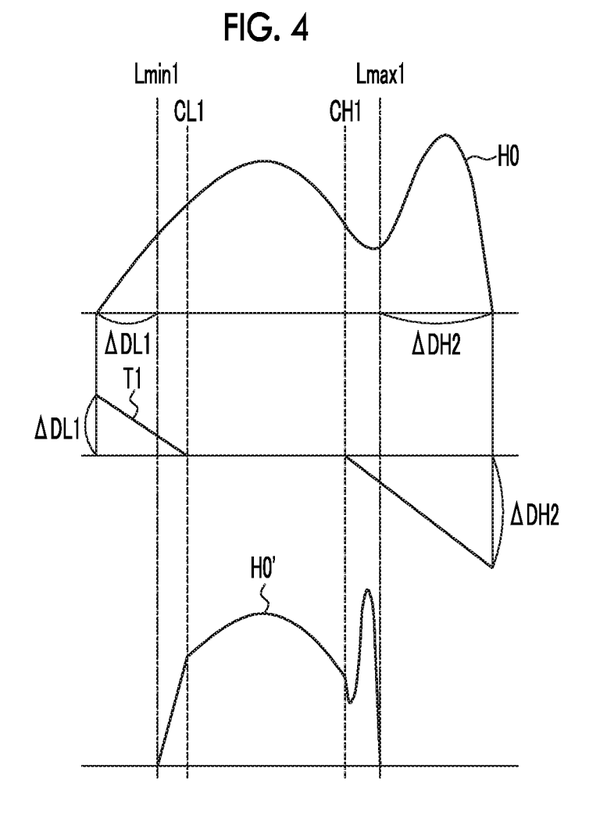
FIG. 4 is a diagram illustrating the generation of a compression table.

The compression table generation unit 34 generates a compression table for compressing the dynamic range of the radiological image G0 on the basis of the first concentration range and the output concentration range. FIG. 4 is a diagram illustrating the generation of the compression table. As illustrated in FIG. 4, the compression table generation unit 34 sets the minimum value CL1 and the maximum value CH1 of the first concentration range and the minimum value Lmin1 and the maximum value Lmax1 of the output concentration range in the histogram H0. The compression table generation unit 34 generates a compression table T1 for compressing a concentration range from the minimum value of the histogram H0 to the minimum value CL1 of the first concentration range and a concentration range from the maximum value of the histogram H0 to the maximum value CH1 of the first concentration range. The compression table T1 is generated such that a concentration width $\Delta DL1$ from the minimum value of the histogram H0 to the minimum value Lmin1 of the output concentration range is compressed on the low concentration side and a concentration width $\Delta DH1$ from the maximum value of the histogram H0 to the maximum value Lmax1 of the output concentration range is compressed on the high concentration side. FIG. 4 also illustrates a histogram H0' of a radiological image G1 after the dynamic range compression process is performed using the generated compression table T1.

In a case in which a general monitor is used, it is difficult for the human to visually recognize a difference in concentration between colors at the minimum value of the concentration which can be displayed by a monitor even if there is a little difference between concentration values and the colors seem to be black. In addition, it is difficult for the human to visually recognize a difference in concentration between colors at the maximum value of concentration which can be displayed by the monitor even if there is a little difference between concentration values and the colors seem to be white. In a concentration range (that is, the concentration range of gray) in the vicinity of the concentration which can be displayed by the monitor, it is easy for the human to visually recognize a difference in density between colors even if there is a small difference between concentration values.

Therefore, on the low concentration side, instead of compressing the concentration width ΔDL1 from the minimum value of the histogram H0 to the minimum value Lmin1 of the output concentration range, the concentration width may be extended from the minimum value of the histogram H0 to a value that is greater than the minimum value Lmin1 of the output concentration range by a predetermined value (about 10%) and then compressed. In addition, on the high concentration side, the concentration width may be extended from the maximum value of the histogram H0 to a value that is less than the maximum value Lmax1 of the output concentration range by a predetermined value (about 10%) and then compressed.

Here, the input unit 5 receives the output concentration range, that is, the L value which is changed by the user. At that time, the processing unit 37 compresses the dynamic range of the radiological image G0, using the compression table T1, acquires a compressed radiological image G1, and displays the compressed radiological image G1 on the display unit 6, which will be described below. The user observes the displayed radiological image G1 and changes the output concentration range, that is, the L value, if necessary. Here, in a case in which the user wants to increase contrast, the user decreases the L value. In a case in which the user wants to decreases contrast or in which blown-out highlights or blocked-up shadows appear, the user increases the L value.

Figure 5:
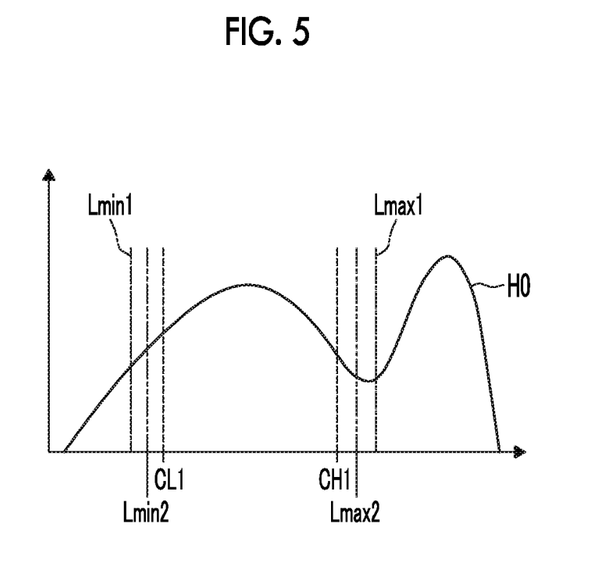
FIG. 5 is a diagram illustrating the determination of a second concentration range.
Figure 6:
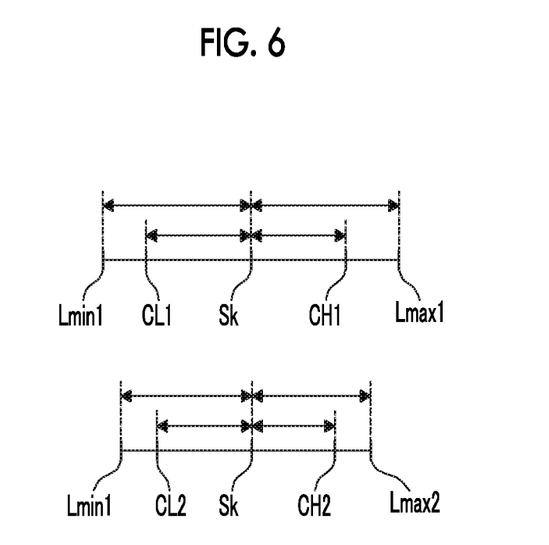
FIG. 6 is a diagram illustrating the determination of the second concentration range.

The second concentration range determination unit 36 changes the first concentration range at a predetermined ratio with respect to the changed output concentration range to determine a second concentration range. Next, the determination of the second concentration range will be described. FIGS. 5 and 6 are diagrams illustrating the determination of the second concentration range. In this embodiment, as illustrated in FIG. 5, it is assumed that the user inputs an instruction to narrow the output concentration range, using the input unit 5, in order to increase contrast. First, the second concentration range determination unit 36 determines a reference concentration, which is a standard for calculating the second concentration range, as the median Sk (hereinafter, simply referred to as Sk) of the output concentration range, that is, the L value. Then, as illustrated in FIG. 6, the second concentration range determination unit 36 determines the minimum value CL2 of the second concentration range on the basis of Sk such that the ratio of Sk-CL1 to Sk-Lmin1 is equal to the ratio of Sk-CL2 to Sk-Lmin2. In addition, the second concentration range determination unit 36 determines the maximum value CH2 of the second concentration range on the basis of Sk such that the ratio of CH1-Sk to Lmax1-Sk is equal to the ratio of CH2-Sk to Lmax2-Sk. That is, the second concentration range determination unit 36 determines the minimum value CL2 and the maximum value CH2 of the second concentration range so as to satisfy the following Expressions (1) and (2).

$$(Sk-CL1)/(Sk-Lmin1)=(Sk-CL2)/(Sk-Lmin2) \quad (1)$$

$$(CH1-Sk)/(Lmax1-Sk)=(CH2-Sk)/(Lmax2-Sk) \quad (2)$$

Figure 7:
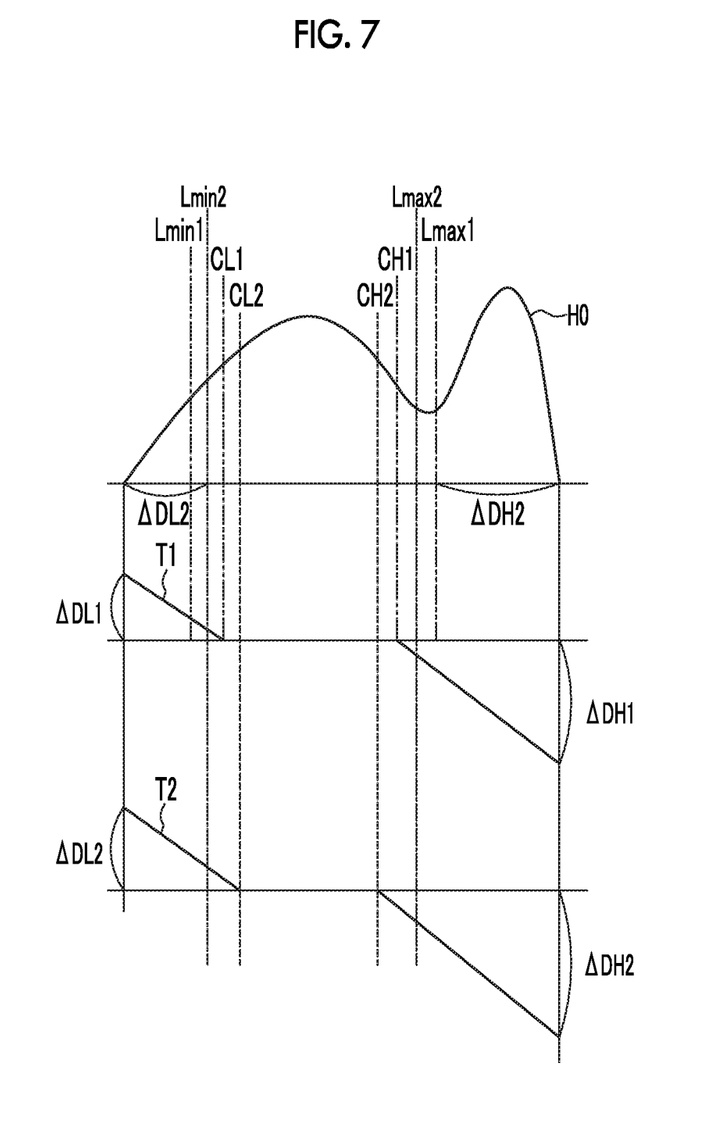
FIG. 7 is a diagram illustrating the generation of a new compression table.

When the second concentration range is determined in this way, the compression table generation unit 34 generates a compression table again. FIG. 7 is a diagram illustrating the generation of the compression table after the second concentration range is determined. As illustrated in FIG. 7, the compression table generation unit 34 sets the minimum value CL2 and the maximum value CH2 of the second concentration range and the minimum value Lmin2 and the maximum value Lmax2 of the changed output concentration range in the histogram H0. The compression table generation unit 34 generates a compression table T2 for compressing a concentration range from the minimum value of the histogram H0 to the minimum value CL2 of the second concentration range and a concentration range from the maximum value of the histogram H0 to the maximum value CH2 of the second concentration range. The compression table T2 is generated such that a concentration width ΔDL2 from the minimum value of the histogram H0 to the minimum value Lmin2 of the output concentration range is compressed on the low concentration side of the radiological image G0 and a concentration width ΔDH2 from the maximum value of the histogram H0 to the maximum value Lmax2 of the output concentration range is compressed on the high concentration side.

The processing unit 37 performs the dynamic range compression process for the radiological image G0, using the compression tables T1 and T2 generated by the compression table generation unit 34. In addition, the processing unit 37 performs other types of image processing, such as a gradation process, a concentration conversion process, and frequency processing, to generate a processed radiological image G1.

Figure 8:
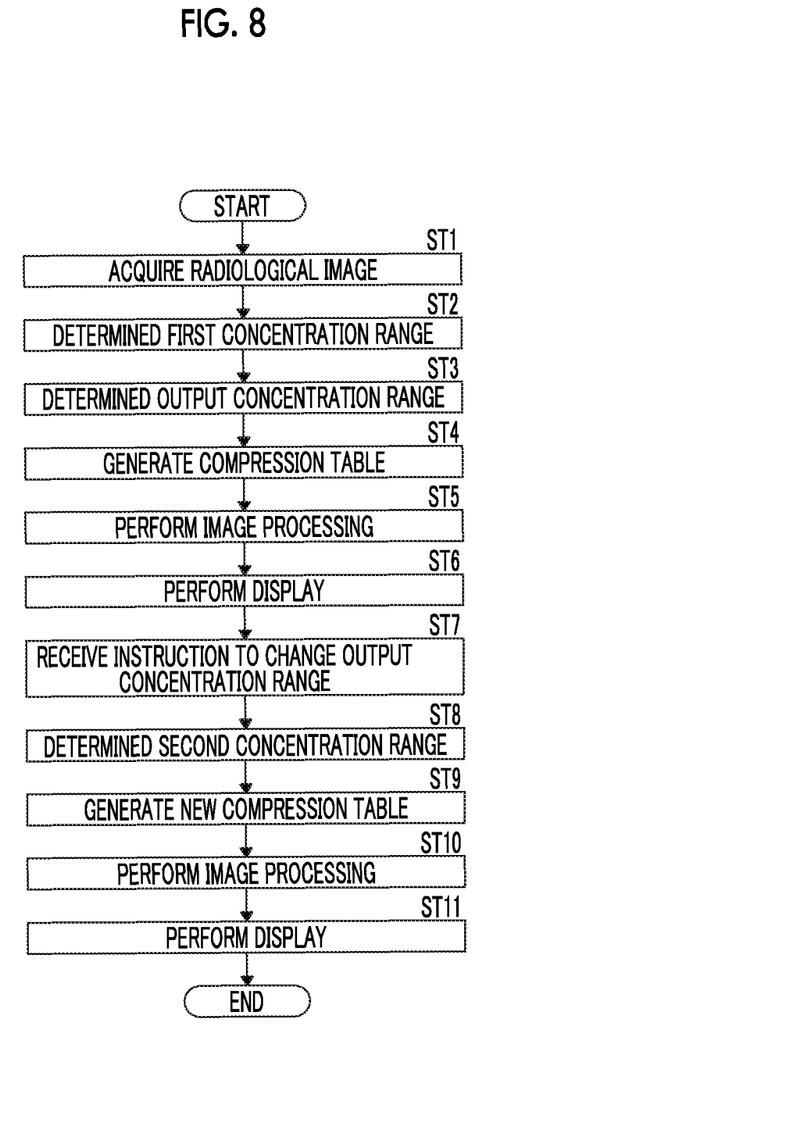
FIG. 8 is a flowchart illustrating a process performed in this embodiment.

Next, a process performed in this embodiment will be described, FIG. 8 is a flowchart illustrating the process performed in this embodiment. It is assumed that the capture of the image of the subject S has been completed. First, the image acquisition unit 31 acquires the radiological image G0 from the radiation detector 2 (Step ST1). The first concentration range determination unit 32 determines the first concentration range which is the concentration range of the region of interest, specifically, the minimum value CL1 and the maximum value CH1 of the first concentration range in the radiological image G0 (Step ST2). Then, the output concentration range determination unit 33 determines the output concentration range, that is, the L value, in the radiological image G0 (Step ST3). Then, the compression table generation unit 34 generates the compression table T1 on the basis of the first concentration range and the output concentration range (Step ST4). The processing unit 37 performs image processing including the dynamic range compression process for the radiological image G0, using the compression table T1 (Step ST5), and displays the processed radiological image G1 on the display unit 6 (Step ST6).

Then, when the user inputs an instruction to change the output concentration range (Step ST7), the second concentration range determination unit 36 determines the second concentration range, specifically, the minimum value CL2 and the maximum value CH2 of the second concentration range, on the basis of the changed output concentration range, as described above (Step ST8). Then, the compression table generation unit 34 generates a new compression table T2 on the basis of the first concentration range and the output concentration range (Step ST9). The processing unit 37 performs image processing including the dynamic range compression process for the radiological image G0, using the compression table T2, (Step ST10) and displays the processed radiological image G1 on the display unit 6 (Step ST11). Then, the process ends. When an instruction to change the output concentration range is received from the user again, a new compression table may be generated again, if necessary.

As such, according to this embodiment, when the output concentration range is changed, the first concentration range is changed at a predetermined ratio with respect to the changed output concentration range to determine the second concentration range and a new compression table is generated on the basis of the changed output concentration range and the second concentration range. Then, the dynamic range compression process is performed. Therefore, when the user changes only the output concentration range, the concentration range of the region of interest in which the dynamic range is not compressed is changed. As a result, it is possible to reduce the burden of the operation of the user. In addition, since the second concentration range is determined by changing the first concentration range at a predetermined ratio with respect to the changed output concentration range, it is possible to appropriately adjust the concentration balance between the changed output concentration range and the second concentration range, according to a predetermined ratio. Therefore, since the dynamic range of the radiological image G0 is compressed using the new compression table T2, it is possible to optimally adjust the concentration balance between the output concentration range and the concentration range of the region of interest, similarly to the method using the compression table T1 before the change. As a result, it is possible to obtain an image with a desired contrast in which blown-out highlights or blocked-up shadows do not occur.

In particular, as illustrated in Expressions (1) and (2), the predetermined ratio is the ratio of a value from the minimum value CL1 of the first concentration range to the median Sk to a value from the minimum value Lmin1 of the output concentration range to the median Sk and the ratio of a value from the median Sk to the maximum value CH1 of the first concentration range to a value from the median Sk to the maximum value Lmax1 of the output concentration range. Therefore, the concentration balance between the changed output concentration range and the second concentration range can be the same as the concentration balance between the output concentration range before a change and the first concentration range. As a result, it is possible to optimally adjust the concentration balance between the output concentration range and the concentration range of the region of interest and thus to obtain an image with a desired contrast.

In the above-described embodiment, the second concentration range is determined on the basis of the median Sk of the L value. However, the second concentration range may be determined on the basis of the minimum value Lmin1 and the maximum value Lmax1 of the output concentration range and the minimum value Lmin2 and the maximum value Lmax2 of the changed output concentration range. In this case, the minimum value CL2 of the second concentration range is determined such that the ratio of CL1-Lmin1 to Lmax1-Lmin1 based on the minimum value Lmin1 and the maximum value Lmax1 is equal to the ratio of CL2-Lmin2 to Lmax2-Lmin2 based on the minimum value Lmin2 and the maximum value Lmax2. In addition, the maximum value CH2 of the second concentration range is determined such that the ratio of Lmax1-CH1 to Lmax1-Lmin1 based on the minimum value Lmin1 and the maximum value Lmax1 is equal to the ratio of Lmax2-CH2 to Lmax2-Lmin2 based on the minimum value Lmin2 and the maximum value Lmax2. That is, the minimum value CL2 and the maximum value CH2 of the second concentration range are determined so as to satisfy the following Expressions (3) and (4).

$$(CL1-Lmin1)/(Lmax1-Lmin1)=(CL2-Lmin2)/(Lmax2-Lmin2) \quad (3)$$

$$(Lmax1-CH1)/(Lmax1-Lmin1)=(Lmax2-CH2)/(Lmax2-Lmin2) \quad (4)$$

In addition, the second concentration range may be determined on the basis of the feature amount Din which is the concentration of a reference pixel value for the gradation process included in the image processing performed by the processing unit 37. The reference pixel value means a pixel value which is converted into a target concentration by the gradation process. As such, in a case in which the second concentration range is determined on the basis of the feature amount Din, the minimum value CL2 and the maximum value CH2 of the second concentration range may be determined so as to satisfy the following Expressions (5) and (6).

$$(Din-CL1)/(Din-Lmin1)=(Din-CL2)/(Din-Lmin2) \quad (5)$$

$$(CH1-Din)/(Lmax1-Din)=(CH2-Din)/(Lmax2-Din) \quad (6)$$

Figure 9:
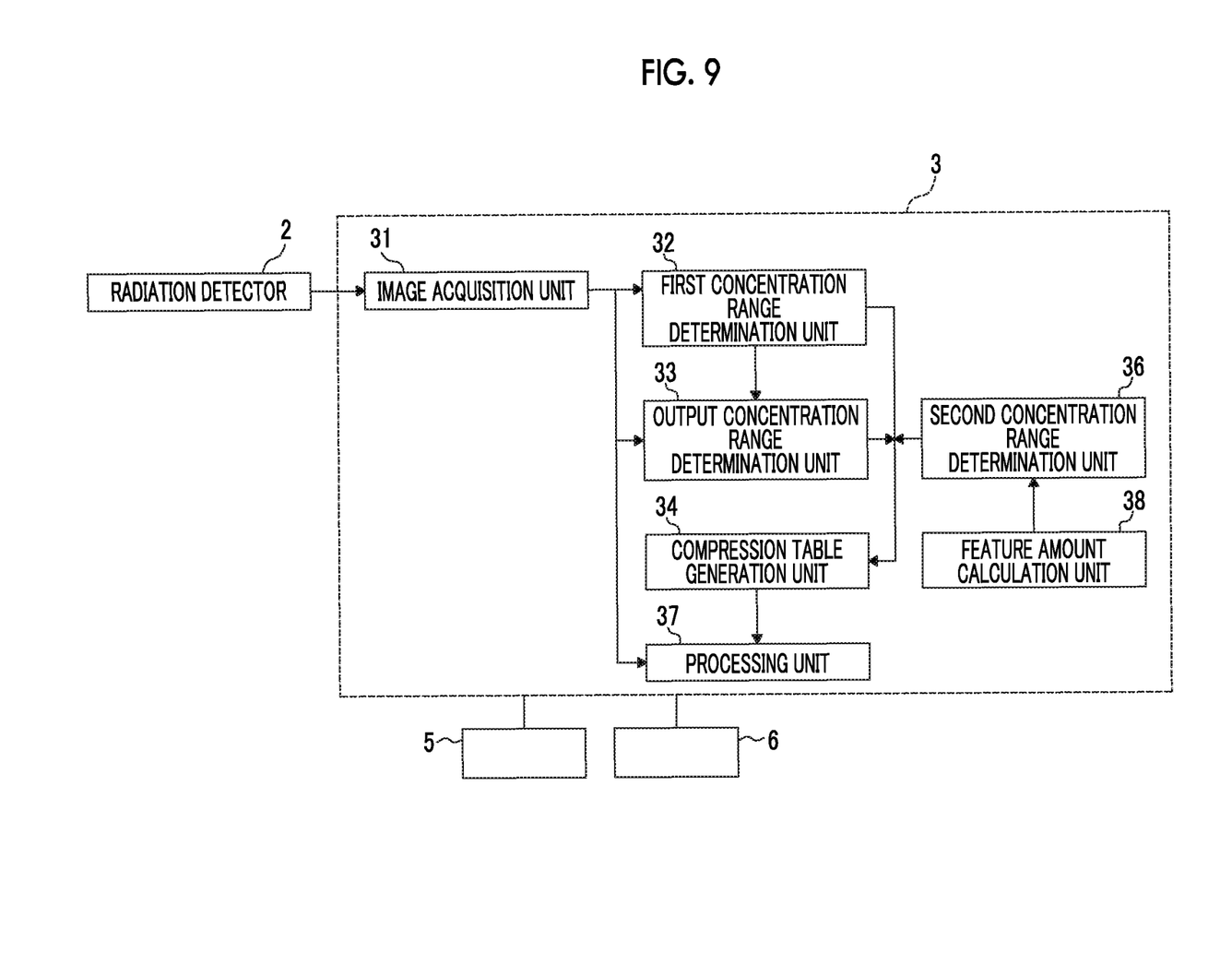
FIG. 9 is a block diagram schematically illustrating another structure of the image processing device.

Here, the user may input the feature amount Din. As illustrated in FIG. 9, the image processing device 3 may be provided with a feature amount calculation unit 38 and the feature amount calculation unit 38 may calculate the feature amount Din. For example, the feature amount calculation unit 38 creates a histogram of the pixel value of the radiological image G0 and calculates the feature amount Din on the basis of the histogram. In this case, for example, the following can be used as the feature amount Din: the mean and median of the histogram; and a value that is less than the maximum value of the histogram by a predetermined percent (for example, 20%) in the entire concentration range of the histogram. In addition, the feature amount Din may be calculated from, for example, information about a captured part.

In addition, preferably, a table in which various captured parts are associated with usage regions is created and stored in advance and a region to be used to calculate the feature amount Din is determined from the information about the captured part.

It may be determined which of the bone part region and the soft part region is used, according to the type of clinical department. For example, in a case in which the radiological image G0 of the chest is captured, an internist observes the state of the lung field and performs a diagnosis and an orthopedist observes the state of the ribs and performs a diagnosis. Therefore, even for the radiological image G0 of the same part, a diagnosis target region varies depending on the clinical department. Here, in a case in which the operator wants to observe the state of the lung field, when the soft part region is determined as the usage region, it is difficult to accurately reproduce a change in the state of the lung field on the processed radiological image. In a case in which the operator wants to observe the state of the bone part, when the bone part region is determined as the usage region, it is difficult to accurately reproduce a change in the state of the ribs on the processed radiological image.

Therefore, the type of clinical department may be acquired as supplementary information and the usage region may be determined on the basis of the part of which the image is to be captured and the type of clinical department. Specifically, in a case in which the clinical department is the internal department, the bone part region may be determined as the usage region in the captured radiological image G0 of the chest. In a case in which the clinical department is orthopedics, the soft part region may be determined as the usage region in the captured radiological image G0 of the chest. In this case, for the same radiological image of the chest, the internist can accurately observe the state of the lung field and the orthopedist can accurately observe the state of the ribs.

In the above-described embodiment, the radiation detector 2 is used to acquire the radiological image of the subject S. However, the radiological image may be acquired using a stimulable phosphor sheet using a stimulable phosphor which stores a portion of radiation energy obtained by the irradiation of radiation and emits stimulable light corresponding to the stored radiation energy when being irradiated with excitation light such as visible light or laser light. In a case in which the stimulable phosphor sheet is used, the stimulable phosphor sheet is irradiated with radiation which has passed through the subject and radiological image information is stored and recorded on the stimulable phosphor sheet. Then, when the storage phosphor sheet is irradiated with excitation light, stimulable light is emitted and is then converted into an electric signal to acquire the radiological image.

In the above-described embodiment, the dynamic range compression process is performed for the radiological image. However, the invention can be applied to a case in which the dynamic range compression process is performed for an image acquired by, for example, a digital camera.

What is claimed is:

1. An image processing device that performs a dynamic range compression process for an input image, comprising:
   a memory storing computer executable instructions; and
   a processor configured to execute the stored instructions, which when executed by the processor cause the processor to perform the following operations:
      determining a first concentration range which is a concentration range of a region of interest in the input image;
      determining an output concentration range in the input image;
      generating a compression table for compressing a dynamic range of the input image on the basis of the first concentration range and the output concentration range;
      compressing the dynamic range of the input image using the compression table;
      receiving an instruction to change the output concentration range;
      changing the first concentration range at a predetermined ratio with respect to the changed output concentration range to determine a second concentration range;
      generating a new compression table on the basis of the changed output concentration range and the second concentration range; and
      compressing the dynamic range of the input image using the new compression table:
   wherein the determining function determines the second concentration range on the basis of a predetermined reference concentration, and
   wherein the predetermined ratio is at least one of a ratio of a value from a minimum value of the first concentration range to the predetermined reference concentration to a value from a minimum value of the output concentration range to the predetermined reference concentration and a ratio of a value from the predetermined reference concentration to a maximum value of the first concentration range to a value from the predetermined reference concentration to a maximum value of the output concentration range.

2. The image processing device according to claim 1, wherein the predetermined reference concentration is a concentration value which is changed to a target concentration in the input image.

3. An image processing device that performs a dynamic range compression process for an input image, comprising:
   a memory storing computer executable instructions; and
   a processor configured to execute the stored instructions, which when executed by the processor cause the processor to perform the following operations:
      determining a first concentration range which is a concentration range of a region of interest in the input image;
      determining an output concentration range in the input image;
      generating a compression table for compressing a dynamic range of the input image on the basis of the first concentration range and the output concentration range;
      compressing the dynamic range of the input image using the compression table;
      receiving an instruction to change the output concentration range;
      changing the first concentration range at a predetermined ratio with respect to the changed output concentration range to determine a second concentration range;
      generating a new compression table on the basis of the changed output concentration range and the second concentration range; and
      compressing the dynamic range of the input image using the new compression table:
   wherein the determining function determines the second concentration range on the basis of a predetermined reference concentration, and
   wherein the predetermined reference concentration is a median of the output concentration range.

4. An image processing method that performs a dynamic range compression process for an input image, comprising:
   determining a first concentration range which is a concentration range of a region of interest in the input image;
   determining an output concentration range in the input image;
   generating a compression table for compressing a dynamic range of the input image on the basis of the first concentration range and the output concentration range;
   compressing the dynamic range of the input image using the compression table;
   receiving an instruction to change the output concentration range;

changing the first concentration range at a predetermined ratio with respect to the changed output concentration range to determine a second concentration range;

generating a new compression table on the basis of the changed output concentration range and the second concentration range; and compressing the dynamic range of the input image using the new compression table, wherein the determining step determines the second concentration range on the basis of a predetermined reference concentration, and wherein the predetermined ratio is at least one of a ratio of a value from a minimum value of the first concentration range to the predetermined reference concentration to a value from a minimum value of the output concentration range to the predetermined reference concentration and a ratio of a value from the predetermined reference concentration to a maximum value of the first concentration range to a value from the predetermined reference concentration to a maximum value of the output concentration range.

5. A non-transitory recording medium having stored therein a program for causing a computer to execute an image processing method that performs a dynamic range compression process for an input image, the program causing the computer to execute the procedures of:

determining a first concentration range which is a concentration range of a region of interest in the input image;

determining an output concentration range in the input image;

generating a compression table for compressing a dynamic range of the input image on the basis of the first concentration range and the output concentration range;

compressing the dynamic range of the input image using the compression table;

receiving an instruction to change the output concentration range;

changing the first concentration range at a predetermined ratio with respect to the changed output concentration range to determine a second concentration range;

generating a new compression table on the basis of the changed output concentration range and the second concentration range; and compressing the dynamic range of the input image using the new compression table, wherein the determining procedure determines the second concentration range on the basis of a predetermined reference concentration, and wherein the predetermined ratio is at least one of a ratio of a value from a minimum value of the first concentration range to the predetermined reference concentration to a value from a minimum value of the output concentration range to the predetermined reference concentration and a ratio of a value from the predetermined reference concentration to a maximum value of the first concentration range to a value from the predetermined reference concentration to a maximum value of the output concentration range.

6. An image processing method that performs a dynamic range compression process for an input image, comprising:

determining a first concentration range which is a concentration range of a region of interest in the input image;

determining an output concentration range in the input image;

generating a compression table for compressing a dynamic range of the input image on the basis of the first concentration range and the output concentration range;

compressing the dynamic range of the input image using the compression table;

receiving an instruction to change the output concentration range;

changing the first concentration range at a predetermined ratio with respect to the changed output concentration range to determine a second concentration range;

generating a new compression table on the basis of the changed output concentration range and the second concentration range; and compressing the dynamic range of the input image using the new compression table, wherein the determining step determines the second concentration range on the basis of a predetermined reference concentration, and wherein the predetermined reference concentration is a median of the output concentration range.

7. A non-transitory recording medium having stored therein a program for causing a computer to execute an image processing method that performs a dynamic range compression process for an input image, the program causing the computer to execute the procedures of:

determining a first concentration range which is a concentration range of a region of interest in the input image;

determining an output concentration range in the input image;

generating a compression table for compressing a dynamic range of the input image on the basis of the first concentration range and the output concentration range;

compressing the dynamic range of the input image using the compression table;

receiving an instruction to change the output concentration range;

changing the first concentration range at a predetermined ratio with respect to the changed output concentration range to determine a second concentration range;

generating a new compression table on the basis of the changed output concentration range and the second concentration range; and compressing the dynamic range of the input image using the new compression table, wherein the determining procedure determines the second concentration range on the basis of a predetermined reference concentration, and wherein the predetermined reference concentration is a median of the output concentration range.

* * * * *